United States Patent [19]
Nguyen

[11] Patent Number: 6,000,082
[45] Date of Patent: Dec. 14, 1999

[54] METHOD FOR MAKING A CUSTOMIZED ORTHOPEDIC SOLE-INSERT

[76] Inventor: Tim The Nguyen, 1768 Via Aracena, Camarillo, Calif. 93010

[21] Appl. No.: 09/250,954

[22] Filed: Feb. 16, 1999

[51] Int. Cl.[6] .............................. A43D 21/00; A61F 5/14
[52] U.S. Cl. ........................ 12/142 N; 12/146 M; 36/140
[58] Field of Search ........................... 12/142 N, 146 M; 36/81, 88, 140, 141, 43, 44

[56] References Cited

U.S. PATENT DOCUMENTS

| | | | |
|---|---|---|---|
| 1,044,015 | 11/1912 | Byrne. | |
| 4,075,772 | 2/1978 | Sicurella | 36/43 |
| 4,223,455 | 9/1980 | Vermeulen | 36/29 |
| 4,876,758 | 10/1989 | Rolloff et al. | 12/146 M |
| 5,027,461 | 7/1991 | Cumberland | 12/146 M |
| 5,493,791 | 2/1996 | Kramer | 36/28 |

*Primary Examiner*—M. D. Patterson
*Attorney, Agent, or Firm*—Ralph D. Chabot

[57] ABSTRACT

A method for making a customized orthotic device utilizing a pre-made sole having a plurality of elongated members extending from the bottom of the sole and inserting each of the elongated members into apertures of a cutting device. Once inserted through the apertures, the distal tips of the elongated members contact a resistance layer which resists the downward movement of the elongated members. A person's foot is then rested on the topside surface of the insert; thereby depressing the insert and elongated member tips into the resistance layer. The compressive force of the foot against the resistance layer tends to conform the insert about the plantar aspect of the foot. A cutting mechanism is then used to cut the elongated members. The finished product, is customized to the foot of the person and is ready to be inserted into a shoe.

15 Claims, 3 Drawing Sheets

U.S. Patent  Dec. 14, 1999  Sheet 1 of 3  6,000,082
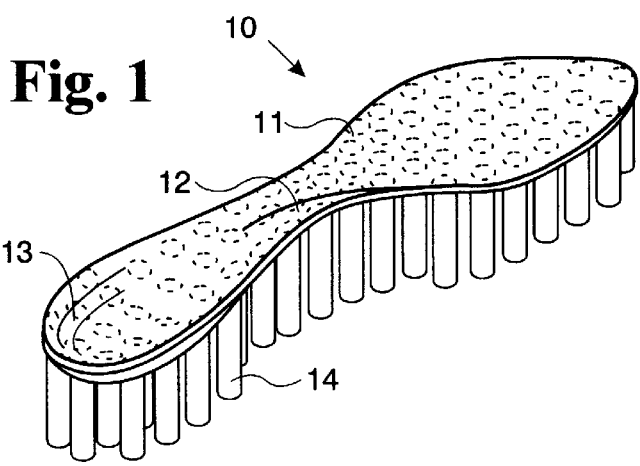
Fig. 1
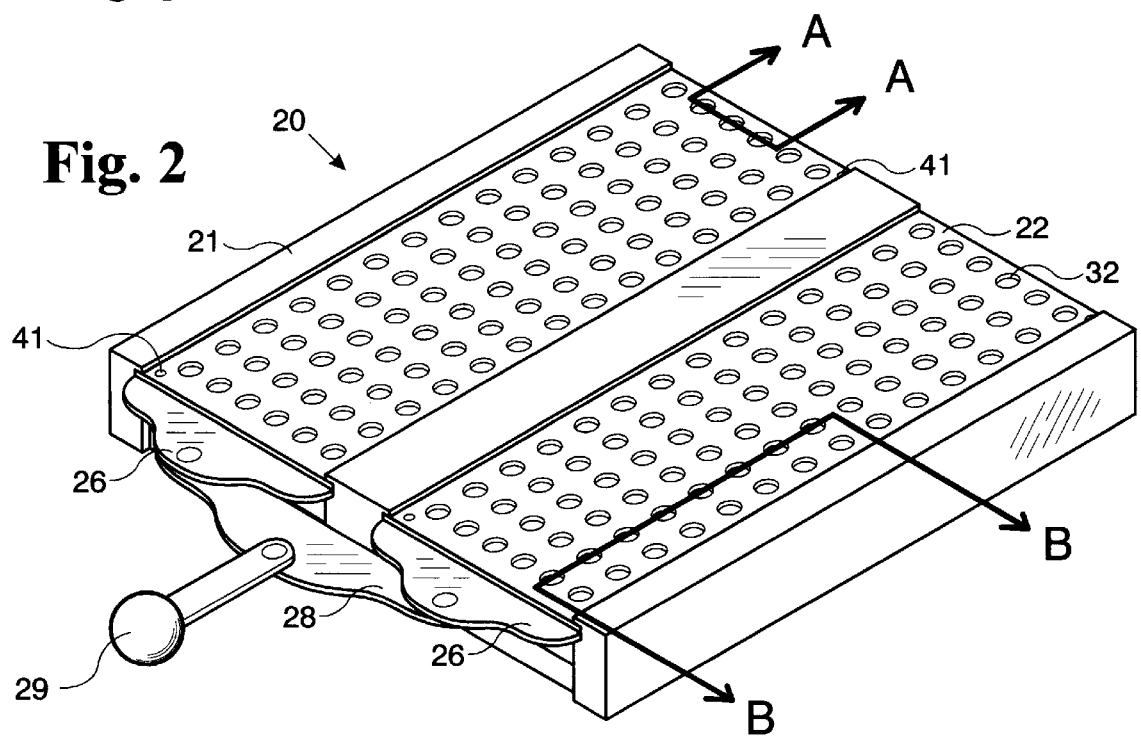
Fig. 2
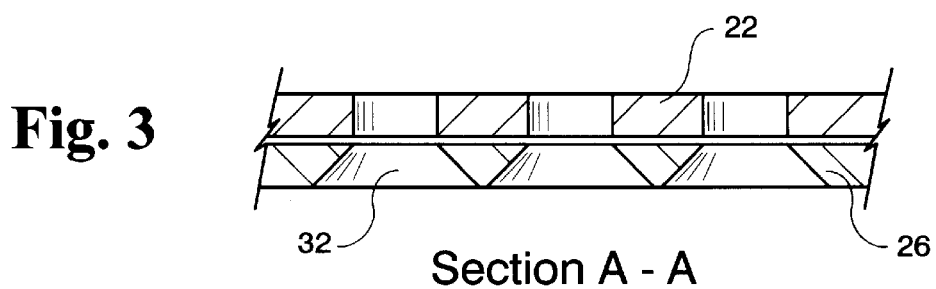
Fig. 3  Section A - A Section B - B

METHOD FOR MAKING A CUSTOMIZED ORTHOPEDIC SOLE-INSERT

BACKGROUND OF THE INVENTION

This invention relates to orthopedic inserts for a shoe and a method to customize the insert for a particular user quickly and efficiently.

The human foot is a unique structure that can be very flexible or very rigid when a person walks depending upon the internal locking and unlocking mechanism of the bones and joints in the person's foot.

This mechanism will not function properly if the bones and joints of the person's foot and ankle are in abnormal alignment. If such an abnormal alignment is present, muscles in the lower extremities will be required to work harder to control the alignment of bones and joints. As a consequence, these muscles become fatigued much quicker resulting in pain and discomfort than if the person had normal alignment.

In response to this problem, there have been many developments in the prior art to correct this problem. Besides surgery, shoe-inserts have been developed. These inserts are positioned between the bottom or plantar aspect of a person's foot and the shoe. The custom sole shoe-insert supports the bones and joints to maintain the normal alignment and redistributes the pressure exerted by a person's body weight upon the plantar aspect of the foot so that the person can walk with greater stability and in more comfort.

A typical method in the prior art is to make a plaster cast of the foot of a person or patient and then have a customized insert manufactured based upon the plaster cast along with any required modifications according to the specific needs of the patient as determined by the attending podiatrist. This type of procedure is expensive, and requires a substantial amount of time between the initial plaster cast and the final product; sometimes on the order of weeks.

The result is that a patient must endure the pain of improper alignment until the insert is completed. Also, due to the expense, a patient normally can not afford additional inserts and will use the same insert when wearing different shoes.

BRIEF SUMMARY OF THE INVENTION

As used in my specification, the terms patient, user, wearer, and person are interchangeable and have the same meaning.

The objects of my invention are as follows:
1. To provide a method of customizing an insert for a patient quickly;
2. To provide an insert which can be customized to the specific needs and requirements of a patient.
3. To provide an insert which is not expensive to manufacture so a user may be able to afford additional inserts for different shoes;
4. Supervision of a podiatrist is not necessary and the insert can be customized at stores where shoes are sold.

My invention begins with a pre-made sole shoe insert having a contoured arch. In the preferred embodiment, a contoured heel cup is also integrated into the pre-made sole shoe insert. The heel seat can range from 3–20 millimeters deep when measured from the edge or lip surface down to the flat horizontal portion of the base or sole surface. The sole also has a plurality of sprouts or elongated members which extend away from the bottom of the sole insert. Preferably, each sprout is integral with the pre-made sole insert. The sprouts can be arranged in various patterns such as linear, circular and elliptical. These sprouts are in various lengths ranging from about 0.25 inch to over 1.5 inch. The diameter of the sprouts are preferred to be in the range of from 0.2–0.7 centimeters. The sprout lengths can be uniform but preferably are shorter where the insert will receive more compressive force such as at the heel or balls of the foot. Preferably, the arch area of the foot will have the longer sprout lengths and sprouts will also be present in the heel portion but not to the length as in the arch area. Also, the end of each sprout can be tapered to permit easier insertion into a cutting device as will be discussed in detail later.

The pre-made sole can be made from various plastic material. Soles can be manufactured of plastics having different degrees of rigidity. In other words, soles can be made from either hard or soft plastic to suit the desired comfort for the wearer. Of particular importance is that the sprouts be sufficiently sturdy to withstand the compressive force of a person's body weight and not buckle after they are cut as will be described later.

The pre-made soles are manufactured in different sizes and widths for proper fit within shoes of varied size and width.

Therefore, the pre-made soles are manufactured with a contoured arch and have a plurality of sprouts extending away from the sole bottom. These pre-made soles are made in various sizes and widths and can be manufactured from different material such as hard or soft plastic. However, each of these pre-made soles are not yet in a condition to be used immediately by a wearer.

The first step is to select the proper size and width of pre-made sole to best fit the wearer. Next, the sprouts are cut according to the contour of the plantar aspect of the foot while the foot is maintained in its neutral position in a partial or total non-weight bearing position. Neutral position of the foot here is defined as the normal alignment which will permit normal range of motion. The sprouts are cut by inserting each sprout of the pre-made sole into a respective aperture of a cutting device or mechanism. As the sprout ends pass through the apertures, they eventually contact the top surface of a resistance medium. Preferably, the resistance medium is a block of foam rubber or the like. Its purpose is to offer some resistance to the downward displacement of the sprouts as the foot is resting on the insert. Accordingly, my invention is not limited to the use of foam rubber as a medium and any means by which a resistance to the downward displacement of the sprouts while the foot is resting on the insert is contemplated to be covered by my invention.

The wearer then positions his foot on the pre-made sole. Preferably, this is done as the wearer is seated, so as not to place the entire body weight upon the sole surface. However, for lighter weight individuals, standing on the insert is acceptable. As the wearer's foot is on the insert, his weight displaces the sprouts further into the cutting mechanism according to the compressive force exhibited on each sprout by the area of the foot directly above the sprout. The resistance medium therefore provides a means to conform the insert to the bottom of the wearer's foot. The sprout lengths are then cut resulting in a customized sole having a plurality of sprouts each having a customized length to provide maximum support to the user.

A higher number of sprouts having smaller diameters is more desirable than fewer sprouts having larger diameters. However, since it is preferred to cut each sprout at the same time, there is a limitation on how small the sprout diameters can be and still be able to cut each sprout at the same time.

The tips of each sprout can also be tapered to permit an easier insertion into the cutting device as will be discussed below.

The following describes the cutting unit and the configuration of the cutting blades. Preferably, the cutting unit is large enough to allow a person to rest both feet on the unit; although a cutting unit having space to cut one sole at a time can be utilized. Under each foot would be a separate cutting device and the following embodiments are part of my inventive concept.

First Embodiment

My cutting device is made of two flat sheets of metal, 15×30 centimeters held in relationship to each other by a metal frame. The top sheet is between 2–10 millimeters in thickness, held firmly to the frame by screws or other fixing means. The bottom sheet thickness can vary from the top sheet but preferably it is also of the same thickness. The bottom sheet however, is capable of sliding back and forth on a pair of rails located on the frame. Each sheet has a plurality of holes or apertures which can be between 0.2 and 10 centimeters in diameter. The holes of the bottom sheet are cone shaped with the smaller side facing the underside of the top sheet. This cone shape is desired to facilitate sharpening of the holes and to allow the cut part of the sprouts to fall off the cutting device more easily. Alternatively, the device will also work with the bottom sheet not having tapered holes and, instead of sharpening the bottom sheet, when the bottom sheet apertures become sufficiently dull, the entire sheet can be replaced with a new sheet having sharp edges about each aperture.

When the slidable bottom sheet is in a first position, its plurality of holes are aligned with the holes of the fixed top sheet thereby creating a common axis of symmetry between each set of holes. The sprouts of the insert are then aligned and inserted into the apertures of the cutting device.

Because the cutting device can be used with various sized inserts, a smaller sized shoe insert will have a smaller number of sprouts than a larger shoe insert having the same diameter-type sprouts. Consequently, not all of the apertures on the cutting device will always be used to receive sprouts.

The cutting mechanism depends on the sheering force between the top and the bottom sheets which also depends on the sheering resistance offered by the sprouts disposed within the apertures. The generated sheering force can be produced by air (pneumatic), hydraulic or electrical power that hammers at the end of the bottom sheet with a strong and quick motion or displacing the bottom sheet by hand by, for example, a bolt and nut mechanism.

The bottom sheet of the cutting device will eventually dull after many uses and will need to be sharpened or replaced. Sharpening of the device can be done by re-smoothing the topside of the bottom sheet by using either a lathe or grinding machine.

The sheet layers can be of any geometric pattern. However, it is preferred to have a rectangular shape so that the cutting device can accommodate different sizes and widths of inserts.

Second Embodiment

Instead of two sheets as in the first embodiment, three sheets are present. The top and bottom sheet are stationary and fixed to the frame and are between 2–10 millimeters in thickness. The middle sheet is slidable and has a thickness of 1–3 millimeters. Each sheet is preferably 6 inches wide by 14 inches long and each sheet has a plurality of holes that have a common axis of symmetry with the corresponding holes of the other sheets.

In this embodiment, the slidable middle sheet is the cutting surface and will eventually either have to be replaced or machined as described for the bottom layer in the first embodiment.

The end layers are fixed in position while the middle layer is moveable. What is most important is that the upper layer, which is the layer closest to the human foot when the foot is positioned on the cutting unit, will not substantially bend or deform under the weight of the user. Such deformation could interfere with the sliding operation of the middle layer to cut the sprouts. This is also true for all other embodiments.

Third Embodiment

This embodiment has three sheets as in the second embodiment except that the second sheet does not have a plurality of holes. Rather, it has a single transverse cutting surface relative to the sprouts and cuts one row of the sprouts at a time as the second sheet is advanced. Behind the edge cutting surface is a flat sheet of metal so that as the blade edge advances, the cut sprouts will be supported by the middle sheet and not descend further into the cutting device. Support of the cut sprouts is desired to maintain the proper weight distribution on the insert while the remaining sprouts are cut.

This embodiment allows easy sharpening of the single flat blade surface and is also able to cut sprouts made of harder material.

Fourth Embodiment

This embodiment has top and bottom sheets which are fixed to the cutting frame as in the second embodiment. The method of cutting the sprouts in this embodiment is with a saw located between the top and bottom sheets which can be powered by hand or electrically. This design allows cutting very hard materials one row at a time. The flat sheet of metal without holes advances forward along with the saw so that the sheet supports the sprouts on a flat level to keep the foot from moving as described in the third embodiment.

Fifth Embodiment

The cutting device can become a locking device using three thin sheets of metal so that once the sprouts have been depressed into a customized position by the foot applying downward force on the insert, the middle sheet is advanced slightly thereby frictionally engaging the sprouts into a fixed position.

The cutting mechanism depends on a grinding machine located just underneath the three sheets to grind off any sprout length exposed below the third sheet. This also allows an opportunity for the technician to check the fitting and comfort on the wearer's foot while the wearer stands with full body weight on the inserts. Also, this design allows a technician to shape the bottom of the device as he wishes so that the bottom surface of the sprouts is not simply limited to a uniform flat surface.

Sixth Embodiment

This embodiment utilizes the same configuration as in the second embodiment except that the surface is curved in a convex shape from heel to toe. This type of cutting surface shape is desired in situations where less pressure under the arch is desired. The curved surface would cut more length from under the arch area so the result would be a customized insert that distributes more weight away from the arch area of the foot.

Operation of the Cutting Unit

The cutting unit is operated as follows:

The sprouts of the pre-made sole are each inserted into a respective aperture. As described above, tapered sprout ends would permit easier insertion into the apertures. The end layers of the cutting device serve to maintain the position of each sprout while they are being cut.

For the bottom layer or sheet of embodiment 1 and the middle layer or sheet of embodiment 2, each aperture on the middle layer provides a cutting edge. Therefore, the middle layer need only be displaced in a horizontal direction the diameter of an aperture to cut all sprouts. It is understood that over continued use, each cutting edge may begin to become dull. In order to provide a simple way to sharpen the cutting edges, each aperture of the middle layer is tapered so that one side has a slightly larger diameter than the other. The cutting edge is defined to be that side of the middle layer having the smaller diameter aperture. This side of the middle layer faces toward the sole and wearer's foot.

When it becomes time to sharpen, the middle layer is removed from the cutting unit and the side having the smaller diameter apertures is uniformly machined or grinded. This reduces the overall thickness of the middle layer but since the aperture holes were originally tapered, reducing the thickness from the side having the smaller diameter apertures creates a new cutting edge for each aperture.

Overall Method to Customize a Sole-Shoe Insert

The person's feet are first examined for size and shape of arch height and a pair of pre-made soles are selected accordingly. The criteria for selection is a pre-made sole with a higher arch than that of the person's and of the same size as the person's shoe size. The pre-made sole is placed on the cutting device with its sprouts passing through respective holes on the device. A block of foam or other material capable of providing slight resistance is placed under the cutting surface. Then the person's foot is placed on the pre-made sole and the foot and ankle are then carefully realigned into a neutral position in partial or non-weight bearing position by a trained technician. The sprouts are then cut by one of the above described embodiments. If less pressure under the arch is desired than the sprouts in this area can be cut with a curved cutting device as described in Embodiment 6 or ground off with a grinding machine as discussed in Embodiment 5.

Occasionally, more rigidity is desired and a flat reinforcing piece in the shape of a foot can be attached to the bottom of the pre-made sole. This flat reinforcing piece has holes or apertures which allow the sprouts extending from the pre-made sole to pass through. Glues or other chemical compounds can also be used to seal the gaps between the flat reinforcing piece and the bottom of the pre-made sole to further increase the rigidity and durability of the insert.

Also, there are several accommodations that can be made to relieve pressure points or transfer the weight distribution of a person on the plantar aspect of his foot. This can be done by increasing or decreasing the height of each sprout manually at any location on the pre-made sole and then cut them to a flat level.

A top layer made of vinyl or cloth material can be attached to the foot-contacting side of the pre-made sole to provide additional comfort to the wearer.

BRIEF DESCRIPTION OF THE DRAWINGS

FIG. 1 is a perspective view of my pre-made insert.

FIG. 2 is a perspective view representation of my two-foot insert cutting device.

FIG. 3 is a view taken along the line A—A of FIG. 2.

DETAILED DESCRIPTION OF THE PREFERRED EMBODIMENT

Figure 12:
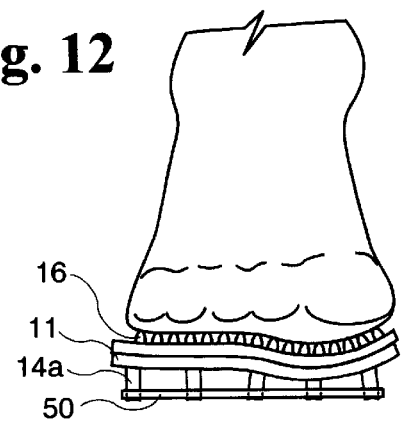
FIG. 12 is the same as FIG. 11 but showing a sole having an additional layer of material for comfort.

The pre-made sole 10 which is part of my invention is illustrated in FIG. 1. It comprises a plastic layer 11 having a contoured arch 12, a countered heel cup 13, and a plurality of elongated elements 14 which I term as sprouts extending from the bottom of layer 11. Contoured heel cup 13 provides increased comfort and stability than if the heel section of sole 10 was not contoured. Sprouts 14 are made of the same plastic material as layer 11 so that layer 11 and sprouts 14 form a single integral piece. Attached to the top of layer 11 can be a layer of cushion material 16 as shown in FIG. 12 to provide comfort and minimize abrasion to the bottom of a wearer's foot.

Various plastic material can be used to form layer 11 and sprouts 14. Critical at this point is the needs of the wearer. In some instances, a firmer, more rigid support is required and a harder plastic is needed. In other situations, a different wearer may require a less rigid support and a softer, more pliable plastic is required.

My invention encompasses the manufacture of various sizes of soles 10. Each size will have various selections according to width and firmness. Although this will result in a multitude of types of soles 10, each sole 10 will have the critical aspect of my invention, that being elongated elements 14.

Figure 8:
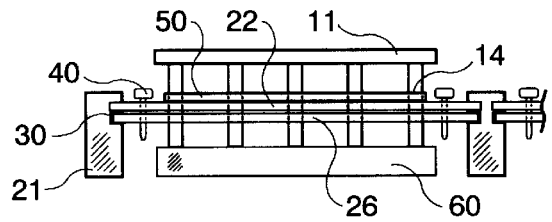
FIG. 8 is a side view of the pre-made insert in relation to the three sheet cutting device embodiment having a resistance means and also employing a reinforcing sole.

A cutting device 20 is required for cutting elongated elements 14. My cutting device is made of two flat sheets of metal 22 and 26 which are held in relationship to each other by metal frame 21. Top sheet 22 is held firmly to frame 21 by screws or other fixing means. Top sheet 22 and bottom sheet 26 are preferably of the same thickness. Bottom sheet 26 however, is capable of sliding back and forth on a pair of rails 30 located on frame 21 as best shown in FIG. 8. Each sheet has a plurality of holes or apertures 32. As indicated in FIG. 3, the holes 32 of slidable bottom sheet 26 are cone shaped or tapered with the smaller side facing the underside of top sheet 22. This cone shape is desired to facilitate sharpening of the holes 32 and to allow the cut part of the sprouts to fall off the cutting device more easily.

Alternatively, bottom sheet 26 can be made without tapered holes and, instead of sharpening bottom sheet 26, when apertures 32 of bottom sheet 26 become sufficiently dull, bottom sheet 26 can be replaced with a new bottom sheet having sharp edges about each aperture.

When slidable bottom sheet 26 is in a first position, its plurality of holes 32 are aligned with holes 32 of fixed top sheet 22 thereby creating a common axis of symmetry between each set of holes 32. When slidable layer 26 is in a first position, it can be temporarily held in position by restraining pins 40 placed into holes 41. Sprouts 14 of insert 10 are then aligned and inserted into apertures 32 of cutting device 20.

Occasionally, it may be necessary to provide additional support for sprouts 14a, the cut sprouts remaining part of sole 11 in order to avoid buckling under the weight of a heavy person. For this situation, prior to inserting sprouts 14 into holes 32, a reinforcing sole 50 having a plurality of apertures is provided. Reinforcing sole 50 is made of a rigid plastic material and is sized accordingly to conform with the pre-made sole for size, width and sprout number.

Figure 11:
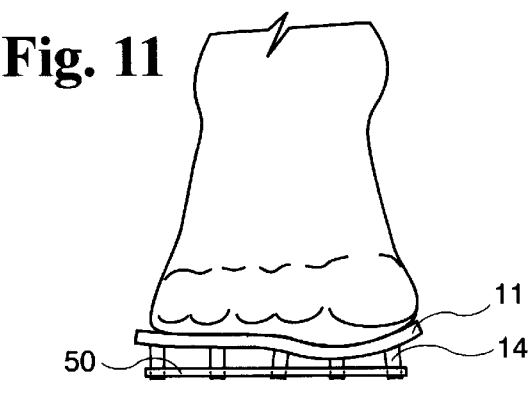
FIG. 11 depicts a insert having a reinforcing sole after being cut by the cutting device.

Sprouts 14 are then inserted through the apertures of reinforcing sole 50 prior to being inserted through holes 32 of cutting device 20. After passing through holes 32, the tips of sprouts 14 will contact a resistance means which, in this embodiment, is a block of foam rubber 60. The purpose of block 60 is to provide some resistance to the complete downward displacement of sprouts 14. A human foot is positioned on the topside of sole 10 and the resistance of block 60 provides a means for contouring plastic layer 11 to the plantar aspect of the wearer's foot. The cutting mechanism is then operated and the end result is shown in FIG. 11. For added support, an epoxy or other type of adhesive or glue can be applied to the void area between plastic layer 11 and reinforcing sole 50 for additional sturdiness.

FIG. 2 illustrates the preferred embodiment in which one or two inserts can be customized for a wearer at the same time. A pair of bottom sheets 26 are connected together by a support member 28 having a handle 29. An operator can then apply a pulling force to handle 29 and bottom sheets 26 are slidably displaced at the same rate and cut sprouts 14 from both inserts 10 while a wearer has positioned both feet on cutting device 20.

Figure 7:
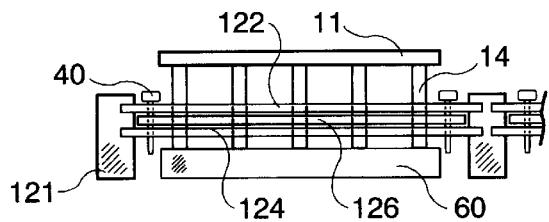
FIG. 7 is a side view of the pre-made insert in relation to the two sheet cutting device embodiment having a resistance means.
Figure 9:
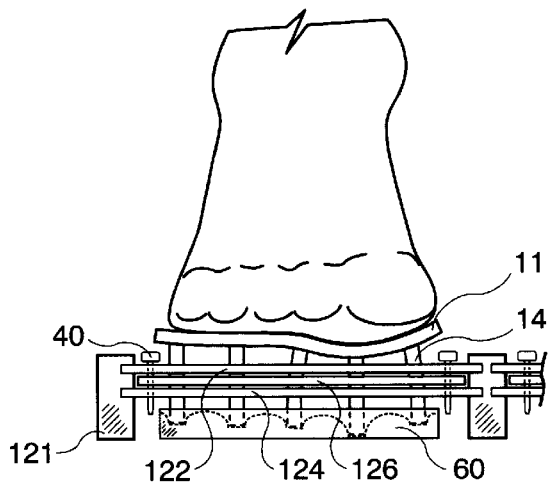
FIG. 9 illustrates the sprout displacement when a foot is applied to the top surface of the insert.
Figure 10:
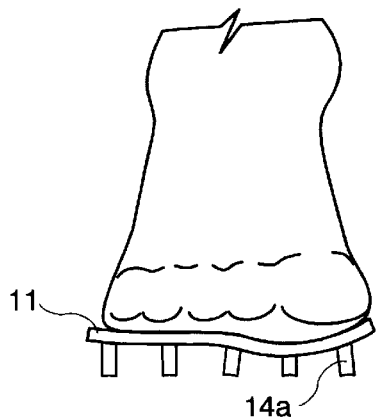
FIG. 10 shows the sprout length after being cut by the cutting device.

In an alternative embodiment as shown in FIG. 7 and FIG. 9, cutting device 20 has three layers 122, 124 and 126. Layers 122 and 124 are stationary with respect to frame 121. Located between layers 122 and 124 is layer 126. Layer 126 is slidable and provides the cutting surface for cutting sprouts 14. Each layer has a plurality of apertures 32 and, when slidable layer 126 is in a first position, it can be temporarily held in position by restraining pins 40. While in this first position, each aperture 32 on each layer has a common axis of symmetry with a respective aperture 32 on each of the other two layers. This is necessary so that sprouts 14 can be partially inserted through the respective apertures in layers 122, 126 and 124.

Layer 122 must be of sufficient rigidity to resist appreciable deformation which could interfere with the cutting operation when a person's weight is on stand 121.

The apertures of slidable layer 126 preferably possess the same taper as described above for layer 26. The cutting surface will be the side of layer 126 having the smaller diameter aperture and this side should be directly facing layer 122.

Figure 4:
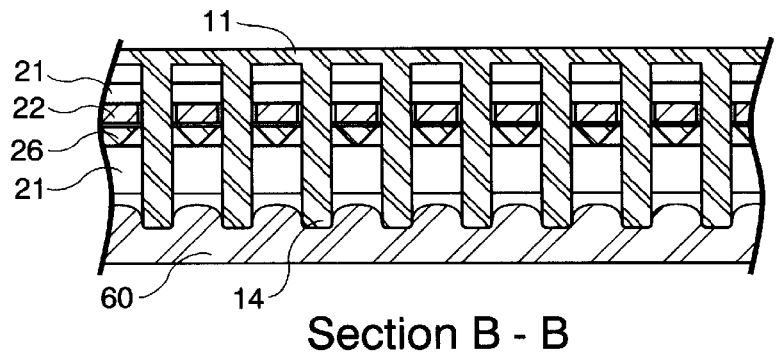
FIG. 4 shows a pre-made insert with sprouts inserted into the view of line B—B of FIG. 2.
Figure 5:
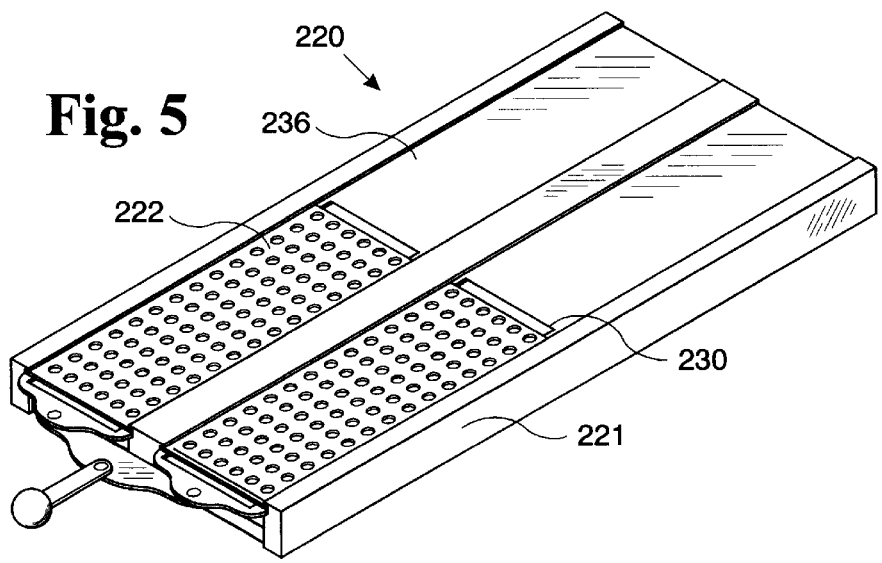
FIG. 5 illustrates an alternative embodiment for a cutting device.
Figure 6:
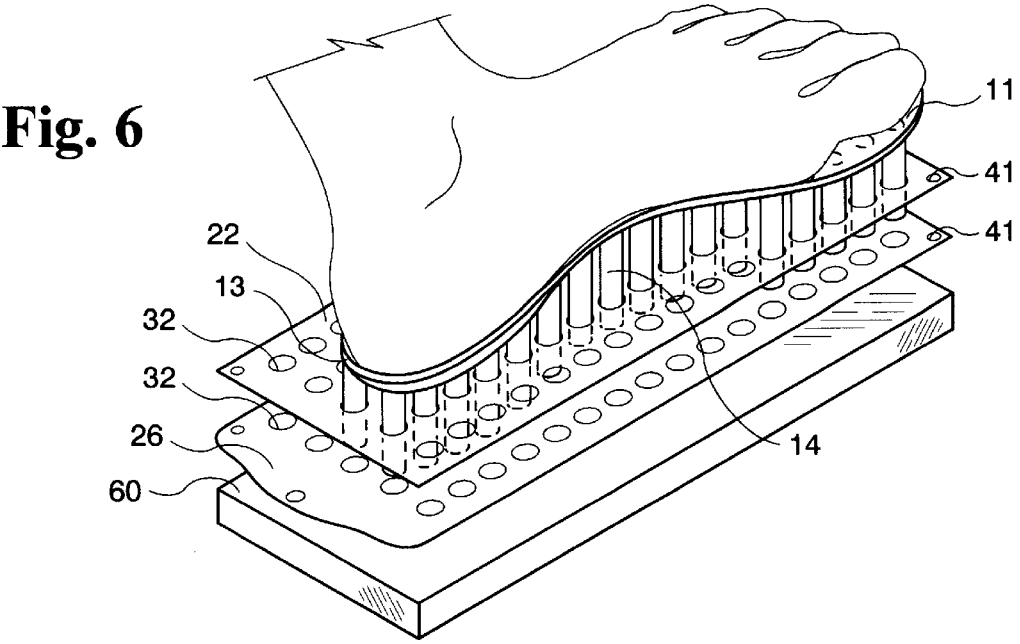
FIG. 6 is an exploded view of the relationship of the foot to the pre-made insert to the cutting device.

FIG. 5 illustrates an additional alternative embodiment which was referred to above as the third embodiment. This cutting device 220 utilizes a sheet of rigid material 222 having a plurality of apertures 232 and a single transverse cutting surface 230 which is the leading edge of a solid sheet of rigid material 236. Sheet 236 is mounted in slidable relation to the frame 221 relative to sheet 222. Sheet 236 is initially positioned so that neither cutting surface 230 nor any portion of sheet 236 is directly below apertures 232. In this initial position, sprouts 14 can be inserted through apertures 232. The same resistance means is utilized as in the other embodiments. After the sprouts have been inserted through apertures 232 and a human foot is properly positioned on the top side of the sole insert, sheet 236 is slid toward sprouts 14 and cuts one row of the sprouts at a time as the sheet 236 is advanced. The cut sprouts 14a will be supported by sheet 236 and not descend further into the cutting device. Support of the cut sprouts is desired to maintain the proper weight distribution on the insert while the remaining sprouts are cut.

This embodiment allows easy sharpening of the single flat blade surface 230.

I claim:

1. A method for producing a customized orthopaedic insert for a specific user comprising the steps of:

providing a pre-made sole having a top side and a bottom side, said sole having a contoured arch and said sole further having a plurality of elongated elements extending away from said bottom side;

providing a cutting device comprising a first and a second sheet of rigid material having a plurality of apertures, said first and second sheets are fixed in position where the apertures of said first sheet have a common axis of symmetry with the corresponding apertures of said second sheet, a slidable third sheet having a plurality of apertures disposed between said first and said second sheets, where initially, said third sheet is in a first position where said third sheet plurality of apertures have a common axis of symmetry with the plurality of apertures of said first and second sheets, and when said third sheet is in said first position, said cutting device is capable of receiving said elongated elements of the pre-made sole through respective apertures such that said elongated elements extend through said second sheet apertures;

providing a resistance means which is capable of resisting the complete downward displacement of said elongated elements of the pre-made sole;

inserting said elongated elements of the pre-made sole through respective apertures of said cutting device;

positioning a human foot upon said pre-made sole so that said contoured arch is aligned with the arch of the human foot and said elongated elements are displaced further through said apertures;

sliding said third sheet from said first position to a second position which will shear off the portion of each of said elongated elements which extend through said apertures of said third sheet; and, removing the pre-made sole from the cutting device.

2. The method of claim 1 wherein said resistance means comprises a block of foam rubber.

3. The method of claim 1 where a pair of cutting devices are used to cut two pre-made soles at the same time.

4. The method of claim 1 wherein the apertures of said third sheet are tapered.

5. The method of claim 1 wherein said pre-made sole further comprises an integral contoured heel section for receiving a human heel therein.

6. A method for producing a customized orthopaedic insert for a specific user comprising the steps of:

providing a pre-made sole having a top side and a bottom side, said sole having a contoured arch and said sole further having a plurality of elongated elements extending away from said bottom side;

providing a cutting device comprising a first sheet of rigid material having a plurality of apertures, said first sheet fixed in position; a slidable second sheet positioned below said first sheet, said second sheet having a plurality of apertures, where initially, said slidable second sheet is in a first position where said second sheet plurality of apertures have a common axis of symmetry with the plurality of apertures of said first sheet, and when said slidable second sheet is in said first position, said cutting device is capable of receiving said elongated elements of the pre-made sole through respective apertures such that said elongated elements extend through said second sheet apertures;

providing a resistance means which is capable of resisting the complete downward displacement of said elongated elements of the pre-made sole;

inserting said elongated elements of the pre-made sole through respective apertures of said cutting device;

positioning a human foot upon said pre-made sole so that said contoured arch is aligned with the arch of the human foot and said elongated elements are displaced further through said apertures;

sliding said second sheet from said first position to a second position which will shear off the portion of each of said elongated elements which extend through said apertures of said third sheet; and, removing the pre-made sole from the cutting device.

7. The method of claim 6 wherein said resistance means comprises a block of foam rubber.

8. The method of claim 6 where a pair of cutting devices are used to cut two pre-made soles at the same time.

9. The method of claim 6 wherein the apertures of said second sheet are tapered.

10. The method of claim 6 wherein said pre-made sole further comprises an integral contoured heel section for receiving a human heel therein.

11. A method for producing an sole insert for a shoe which is customized for the wearer comprising the steps of:

providing a pre-made sole having a top side and a bottom side, said sole having a contoured arch and said sole further having a plurality of elongated elements extending away from said bottom side;

providing a cutting device having at least one sheet of rigid material having a plurality of apertures, and at least one cutting surface located under said sheet, said apertures capable of receiving said elongated elements and the cutting surface capable of cutting the portion of said elongated elements that extend below the cutting surface; said cutting device further incorporates a resistance means which will contact the distal ends of said elongated elements and is capable of resisting the complete downward displacement of said elongated elements of the pre-made sole;

inserting said elongated elements of the pre-made sole through respective apertures of said cutting device;

positioning a human foot upon said pre-made sole so that said contoured arch is aligned with the arch of the human foot and said elongated elements are displaced further through said apertures;

operating the cutting the device to cut the portion of each elongated element which extends below the cutting surface of said cutting device, the sole-insert with the remaining integral lengths of elongated elements defining a customized sole-insert; and removing the customized sole-insert from the cutting device.

12. The method of claim 11 wherein said resistance means comprises a block of foam rubber.

13. The method of claim 11 where a pair of cutting devices are used to cut two pre-made soles at the same time.

14. The method of claim 11 wherein said resistance means comprises a block of foam rubber.

15. The method of claim 11 wherein said pre-made sole further comprises an integral contoured heel section for receiving a human heel therein.

* * * * *